United States Patent [19]
Holliday

[11] Patent Number: 5,840,497
[45] Date of Patent: Nov. 24, 1998

[54] METHOD FOR SPECIFIC SILENCING OF GENES BY DNA METHYLATION

[75] Inventor: Robin Holliday, West Pennant Hills, Australia

[73] Assignee: The Commonwealth of Australia Commonwealth Scientific and Industrial Research Organization, Campbell, Australia

[21] Appl. No.: 937,583

[22] PCT Filed: Jun. 10, 1994

[86] PCT No.: PCT/AU94/00314

§ 371 Date: Feb. 5, 1996

§ 102(e) Date: Feb. 5, 1996

[87] PCT Pub. No.: WO94/29461

PCT Pub. Date: Dec. 22, 1994

Related U.S. Application Data

[63] Continuation of Ser. No. 553,587, Feb. 5, 1996, abandoned.

[30] Foreign Application Priority Data

Jun. 11, 1993 [AU] Australia .................. PL 9338

[51] Int. Cl.$^6$ .............. C12Q 1/68; C07H 21/00; C12N 5/10
[52] U.S. Cl. .............. 435/6; 435/375; 435/325; 514/44; 536/23.1; 536/24.1; 536/24.5; 536/24.3
[58] Field of Search ................. 514/44; 435/6, 435/375, 325; 536/23.1, 24.1, 24.5, 24.3; 935/33

[56] References Cited

FOREIGN PATENT DOCUMENTS

WO 89/08146   9/1989   WIPO .

OTHER PUBLICATIONS

Rojanasakul, Antisense Oligonucleotide Therapeutics: Drug Delivery and Targeting. *Advanced Drug Delivery Reviews*, vol. 18 1996 pp. 115–131.

Robin Holliday et al, Gene Silencing in Mammalian Cells by Uptake of 5–Methyl Deoxycytidine–5'–triphosphate, Somatic Cell Molecular Genetics, vol. 17, No. 6, 1991, pp. 537–542.

Jonathan Nyce, Gene Silencing in Mammalian Cells by Direct Incorporation of Electroporated 5–Methyl–2'–deoxycytidine 5'–triphosphate, Somatic Cell Molecular Genetics, vol. 17, No. 6, 1991, pp. 543–550.

W. French Anderson, Human Gene Therapy, Science, vol. 256, pp. 808–813.

Fritz Eckstein et al, Phosphorothioates in Molecular Biology, TIBS 14, Mar. 1989, pp. 97–100.

*Primary Examiner*—George C. Elliott
*Assistant Examiner*—Sean M. Garry
*Attorney, Agent, or Firm*—McDermott, Will & Emery

[57] ABSTRACT

The present invention provides a method for the silencing of specific genes by DNA methylation. The method involves introducing into a cell a single stranded oligonucleotide containing 5-methyl deoxycytosine. The single stranded oligonucleotide has a sequence complementary to a portion of the DNA sequence of the gene to be silenced.

8 Claims, No Drawings

METHOD FOR SPECIFIC SILENCING OF GENES BY DNA METHYLATION

This application is a continuation of application Ser. No. 08/553,587 filed Feb. 5, 1996, and now abandoned, which is a 371 of PCT/AU94/00314 filed Jun. 10, 1994.

The present invention relates to a method for the silencing of specific genes by DNA methylation. The method involves the introduction into cells of oligonucleotides containing 5-methyl cytosine residues, the oligonucleotide having a sequence complementary to a portion of the DNA of the gene to be silenced.

It is known that the methylation of cytosine in DNA by the enzyme DNA methyl transferase results in the inactivation of gene expression in many biological contexts. Furthermore, once a cytosine residue is methylated in a CpG doublet, the enzyme recognises this substrate after DNA replication and methylates the new strand, whereas non-methylated CpG doublets remain unmethylated. Thus a given pattern of DNA methylation is heritable, and the methylated genes remain silent. Non-specific gene silencing in CHO cells has been achieved by uptake of 5-methyl deoxycytosine triphosphate (Holliday & Ho, 1991, Somatic Cell and Molecular Genetics, 17:537–542; Nyce, 1991, Somatic Cell and Molecular Genetics, 17:543–550). The new method developed by the present inventors can silence specific genes, provided the sequence of bases in the promoter region is known. The method developed by the present inventors involves the use of single stranded oligonucleotides containing 5-methyl deoxycytosine in appropriate CpG doublets.

Accordingly, in a first aspect the present invention consists in a method of silencing a specific gene in a cell comprising introducing into the cell a single stranded oligonucleotide containing 5-methyl deoxycytosine, the single stranded oligonucleotide having a sequence complementary to a portion of the DNA sequence of the gene to be silenced.

In a preferred embodiment of the present invention the single stranded oligonucleotide has a sequence complementary to a sequence within the promoter region of the gene to be silenced or within CpG islands of the gene to be silenced.

As will be readily appreciated provided some or all of the cells are actively synthesising DNA (S phase), the methylated oligonucleotide can anneal or hybridize to single stranded DNA at the replication fork. Accordingly, it is presently preferred that the cells are synchronized and treated during DNA synthesis. Synchrony can be achieved by serum starvation, followed by addition of serum which stimulates DNA synthesis, or other methods of synchronization.

As is clear from the above discussion the method of the present invention depends on the synthesis of single stranded oligonucleotides containing 5-methyl deoxycytosine in appropriate CpG doublets or at other sites. The synthesis is a standard procedure substituting 5-methyl deoxycytosine phosphoroamidate for cytosine phosphoroamidate (ABI systems oligonucleotide synthesiser). The target gene is unmethylated in the promoter region and the gene is, or can be, expressed in the cells to be treated. The oligonucleotide can be introduced into the cells by electroporation, Transfectam or by any other means of permealizing cells or by other methods of introducing DNA into cells. Provided some or all of the cells are actively synthesising DNA (S phase), the methylated oligonucleotide can anneal or hybridize to single stranded DNA at the replication fork. This creates a hemimethylated substrate for the DNA methyltranferase. The enzyme methylates the cellular DNA in the region of hybridization. This methylation imprint in a short region of the promoter silences the specific gene, and the effect is permanent because the methylation is subsequently inherited. In order that the target gene is specifically recognize the oligonucleotide is of sufficient length (20–40 bases) to hybridize only with this gene and no other in the genome. Alternatively, the oligonucleotide could hybridise to the gene during active transcription, because there is some unwinding of the DNA during this process. The end result is the same.

The cells can be primary human cells, or permanent lines of human or animal origin. The cells should be synchronized and treated during DNA synthesis. Synchrony can be achieved by serum starvation, followed by addition of serum which stimulates DNA synthesis, or any alternative method of synchronization can be used.

To detect gene silencing it is desirable or necessary to have a selection procedure which eliminates cells containing the active gene. Many such selection procedures are available including genes which synthesise thymidine kinase, adenine phosphoribosyl transferase and hypoxanthine phosphoribosyl tranferase. There should be only one active copy of the gene to be targeted. Genes of the histocompatibility complex such as HLA-A in human cells produce a cell surface antigen. An appropriate antiserum and complement will kill all cells expressing the antigen. In this case the gene is often heterozygous (e.g. HLA-A2/HLA-A3) and it is possible to select cells which are not expressing either haplotype (e.g. by using antiserum against A2 or A3 antigens). Although the promoter region of both genes may be the same, the methylation of one will eliminate the gene product and such cells can be selected. These can be used in a second treatment with methylated oligonucleotide which can yield cells lacking both surface antigens.

Many inherited human diseases are caused by dominant genes. These may produce an excess of a gene product or an altered gene product. Cells from such individuals could be made normal if the dominant gene can be specifically silenced. This could be done with skin fibroblasts or lymphocytes in vitro, or haematopoietic bone marrow stem cells. In appropriate cases, methylated oligonucleotides could be used to silence specific genes in vivo. These approaches resemble procedures for gene therapy, where a defective recipient gene is converted to a normal gene by uptake and integration of DNA into the chromosome. More information can be obtained regarding gene therapy in W. French Anderson, 1992, "Human Gene Therapy", Science 256, 808–813.

It should also be noted that the oligonucleotides used in the method of the present invention may hybridize to either the sense or antisense strand of DNA.

In order to protect the single stranded oligonucleotide from degradation by nucleases it is presently preferred that methylated phosphorothioate oligonucleotides are used. Further information concerning such oligonucleotides may be found in Eckstein & Gish, 1989, TIBS 14, 97–100.

As will be recognized by those skilled in the art the present invention has a wide number of applications. By silencing the histocompatibility genes "universal" donor cells for use in transplantation can be produced. Indeed, it is foreseeable that a wide range of cells which do not express antigens typically involved in transplantation rejection can be produced. This opens up the possibility of universal donor cells.

An obvious model target to prove the system is the gene coding for HPRT (hypoxanthine phosphoribosyl transferase) because it is X linked, with only one copy in male cells and one active copy in female cells. Cells with an active HPRT gene can grow in HAT medium (containing hypoxanthine, aminopterin and thymidine) but are killed by 6 thioguanine (6TG). Cells without HPRT are resistant to 6TG, but cannot grow in HAT medium. Thus, one can select for loss of enzyme activity following silencing of the gene, and also for gain of activity following reactivation of the gene. Reactivation can be achieved by the demethylating agent 5 azacytidine.

The human, mouse and hamster HPRT genes have been sequenced. They contain 9 exons and very long introns. At the 5' end of the gene is a CpG island, which is normally unmethylated, but which becomes methylated during X chromosome inactivation. The promoter region contains many CpG sites, but there are reasons to believe that important regulatory sites may be in a relatively short stretch of DNA (100–200 nucleotides).

Experiments are carried out with male human fibroblasts, strain MRC-5. Methylated oligonucleotides of 40–50 length covering different regions of the promoter can by synthesized, and prepared for treating the cells.

These will be partially synchronized, following serum deprivation, and treated when the majority are in S phase −20 hours after replacing serum. The cells are allowed 6–8 days expression time to allow pre-existing HPRT to disappear, and then plated on 6TG medium. Colonies appearing will be picked, grown up, and tested for reactivation by azacytidine. Such reactivants can be selected on HAT medium. If no colonies are obtained, oligonucleotides with other sequences in the promoter region will be tested.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

I claim:

1. A method of silencing a specific gene in a cell in vitro comprising introducing into the cell a single stranded oligonucleotide containing 5-methyl deoxycytosine, the single stranded oligonucleotide having a sequence complementary to a sequence within the promoter region of the gene to be silenced, wherein the sequence within the promoter region contains at least one CpG doublet.

2. A method of silencing a specific gene in a cell in vitro comprising introducing into the cell a single stranded oligonucleotide containing 5-methyl deoxycytosine, the single stranded oligonucleotide having a sequence complementary to a sequence within a regulatory site of the gene to be silenced, wherein the sequence within the regulatory site contains at least one CpG doublet.

3. A method of testing for silencing of a gene in a cell comprising:

(a) introducing into the cell a single stranded oligonucleotide containing 5-methyl deoxycytosine, the single stranded oligonucleotide having a sequence complementary to a sequence within the promoter region of the gene to be silenced, wherein the sequence within the promoter region contains at least one CpG doublet;

(b) selecting for loss of gene product activity following silencing of the gene by growth on a selective culture medium; and (c) reactivating the silenced gene with a demethylating agent.

4. A method of testing for silencing of a gene in a cell comprising:

(a) introducing into the cell a single stranded oligonucleotide containing 5-methyl deoxycytosine, the single stranded oligonucleotide having a sequence complementary to a sequence within a regulatory site of the gene to be silenced, wherein the sequence within the regulatory site contains at least one CpG doublet;

(b) selecting for loss of gene product activity following silencing of the gene by growth on a selective culture medium; and (c) reactivating the silenced gene with a demethylating agent.

5. A method according to any one of claims 1, 2, 3, and 4, wherein the single stranded oligonucleotide comprises about 20–40 nucleotides.

6. A method according to any one of claims 1, 2, 3, and 4, wherein the single stranded oligonucleotide is a methylated phosphorothioate oligonucleotide.

7. A method according to any one of claims 1, 2, 3, and 4, wherein the cell is contained within a cell culture, which has been treated so that the cell cycles of each of the cells contained therein are synchronized.

8. A method according to claim 7, wherein the single stranded oligonucleotide is introduced to the cell when the cells contained within the culture are in S phase.

* * * * *